(12) United States Patent
Yoshida

(10) Patent No.: US 10,393,623 B2
(45) Date of Patent: Aug. 27, 2019

(54) ABNORMALITY DIAGNOSIS DEVICE, BEARING, ROTATION DEVICE, INDUSTRIAL MACHINE AND VEHICLE

(71) Applicant: NSK Ltd., Shinagawa-ku, Tokyo (JP)

(72) Inventor: Kazuhiro Yoshida, Fujisawa (JP)

(73) Assignee: NSK LTD., Tokyo (JP)

( * ) Notice: Subject to any disclaimer, the term of this patent is extended or adjusted under 35 U.S.C. 154(b) by 36 days.

(21) Appl. No.: 15/534,282

(22) PCT Filed: Dec. 9, 2015

(86) PCT No.: PCT/JP2015/006145
§ 371 (c)(1),
(2) Date: Jun. 8, 2017

(87) PCT Pub. No.: WO2016/092845
PCT Pub. Date: Jun. 16, 2016

(65) Prior Publication Data
US 2017/0343451 A1 Nov. 30, 2017

(30) Foreign Application Priority Data
Dec. 10, 2014 (JP) .................................. 2014-250033

(51) Int. Cl.
*G01H 1/00* (2006.01)
*G07C 5/08* (2006.01)
(Continued)

(52) U.S. Cl.
CPC .......... *G01M 13/045* (2013.01); *G01H 1/003* (2013.01); *G01H 17/00* (2013.01);
(Continued)

(58) Field of Classification Search
CPC .... G01M 13/045; G01M 17/08; G01H 1/003; G01H 17/00; G07C 5/0808; G01N 2291/2696; F16C 2326/10
See application file for complete search history.

(56) References Cited

U.S. PATENT DOCUMENTS 6,116,089 A  9/2000 El-Ibiary et al.
7,860,663 B2  12/2010 Miyasaka et al.
(Continued)

FOREIGN PATENT DOCUMENTS

CN  101590981 A  12/2009
CN  102597735 A  7/2012
(Continued)

OTHER PUBLICATIONS

International Search Report (PCT/ISA/210) issued in PCT Application No. PCT/JP2015/006145 dated Mar. 8, 2016 with English translation (Four (4) pages).
(Continued)

*Primary Examiner* — Thomas Ingram
(74) *Attorney, Agent, or Firm* — Crowell & Moring LLP

(57) ABSTRACT

There is provided an abnormality diagnosis device, a bearing, a rotation device, an industrial machine, and a vehicle, which are able to discover abnormality early and also set a diagnosis threshold relatively easily. A differential value between an initial frequency component and an actual measurement frequency component is calculated, the differential value is compared to the diagnosis threshold, and abnormality diagnosis for an abnormality diagnosis target is carried out based on the comparison result, where the initial frequency component is a feature frequency component of abnormality of the abnormality diagnosis target in the rotation device, which is extracted from an initial vibration value measured at initial measurement timing while the axle is rotating at setting rotation speed during an operation of the
(Continued)

rotation device, and the actual measurement frequency component is a feature frequency component extracted from an actual measurement vibration value measured at actual measurement timing that is the initial measurement timing or later while the axle is rotating at the setting rotation speed during the operation of the rotation device.

17 Claims, 9 Drawing Sheets

(51) Int. Cl.
    *G01H 17/00*         (2006.01)
    *G01M 17/08*         (2006.01)
    *G01M 13/045*       (2019.01)

(52) U.S. Cl.
    CPC ........... *G01M 17/08* (2013.01); *G07C 5/0808* (2013.01); *F16C 2326/10* (2013.01); *G01N 2291/2696* (2013.01)

(56) References Cited

U.S. PATENT DOCUMENTS

| | | | |
|---|---|---|---|
| 9,423,290 B2* | 8/2016 | Sakaguchi | G01H 1/003 |
| 9,588,015 B2* | 3/2017 | Sako | G01M 13/045 |
| 2008/0234964 A1* | 9/2008 | Miyasaka | G01H 1/003 |
| | | | 702/113 |
| 2011/0016974 A1 | 1/2011 | Wagner | |
| 2012/0272736 A1 | 11/2012 | Griffaton | |

FOREIGN PATENT DOCUMENTS

| | | |
|---|---|---|
| CN | 202676450 U | 1/2013 |
| JP | 54-98439 A | 8/1979 |
| JP | 2006-105956 A | 4/2006 |
| JP | 2011-252753 A | 12/2011 |
| JP | 2012-100434 A | 5/2012 |
| JP | 2012-242336 A | 12/2012 |

OTHER PUBLICATIONS

Japanese-language Written Opinion (PCT/ISA/237) issued in PCT Application No. PCT/JP2015/006145 dated Mar. 8, 2016 (Four (4) pages).

Japanese-language Office Action issued in counterpart Japanese Application No. 2014-250033 dated Mar. 21, 2017 with English translation (Five (5) pages).

International Preliminary Report on Patentability (PCT/IB/338 & PCT/IB/373) issued in PCT Application No. PCT/JP2015/006145 dated Jun. 22, 2017, including English translation (Japanese-language Written Opinion (PCT/ISA/237)) previously submitted on Jun. 8, 2017 (Seven (7) pages).

Extended European Search Report issued in counterpart European Application No. 15866587.7 dated Nov. 7, 2017 (9 pages).

Chinese Office Action issued in Chinese counterpart application No. 201580067296.1 dated Jan. 14, 2019, with partial English translation (Fourteen (14) pages).

\* cited by examiner

ABNORMALITY DIAGNOSIS DEVICE, BEARING, ROTATION DEVICE, INDUSTRIAL MACHINE AND VEHICLE

TECHNICAL FIELD

The present invention relates to abnormality diagnosis of a rotation device configured by including a bearing that supports a rotation shaft.

BACKGROUND ART

Conventionally, as a technology of carrying out abnormality diagnosis of a rotation device that is configured by including a bearing, there has been, for example, a technology disclosed in Patent Literature 1. In this technology, a function of detecting and processing abnormality of a vehicle and a raceway, which is performed in a periodic inspection, is added to an abnormality determining apparatus that determines an abnormality indicating serious accidents such as derailment, overturn, and collision based on detected signals from a sensor unit attached to a railway vehicle.

CITATION LIST

Patent Literature

PTL 1: JP 2012-100434 A

SUMMARY OF INVENTION

Technical Problem

However, in the above-mentioned conventional technology, individual differences of respective target parts such as bearings and wheels are not considered in terms of setting of diagnosis thresholds depending on matters to be avoided. Therefore, when a product is mass-produced, an enormous amount of back data and statistical judgment are required in setting absolute diagnosis thresholds that are common to identical products, and there has been a problem that lots of verification is necessary until appropriate diagnosis thresholds are set.

Therefore, the present invention has been accomplished in light of unsolved problems of such a conventional technology, and aims to provide an abnormality diagnosis device, a bearing, a rotation device, an industrial machine, and a vehicle, which are able to carry out early discovery of abnormality and, at the same time, set a diagnosis threshold relatively easily.

Solution to Problem

In order to solve the above-mentioned problem, an abnormality diagnosis device according to the first aspect of the present invention is provided with a vibration ++ detecting unit detecting vibration generated in a rotation device configured by including a bearing that supports a rotation shaft, a rotation speed detecting unit detecting rotation speed of the rotation shaft, a vibration measuring unit measuring vibration generated in the rotation device while the rotation shaft is rotating at previously set setting rotation speed, based on a detection result of the rotation speed detecting unit and a detection result of the vibration detecting unit, an initial frequency component extraction unit extracting a feature frequency component regarding abnormality of each abnormality diagnosis target of the rotation device, from an initial vibration value, which is a value of the vibration measured by the vibration measuring unit at previously set initial measurement timing while the rotation device is in operation, an actual measurement frequency component extraction unit extracting the feature frequency component of each abnormality diagnosis target from an actual measurement vibration value, which is a value of the vibration measured by the vibration measuring unit at actual measurement timing, which is the previously set initial measurement timing or later, while the rotation device is in operation, a differential value calculating unit calculating a differential value between an initial frequency component, which is the feature frequency component extracted from the initial vibration value, and an actual measurement frequency component, which is the feature frequency component extracted from the actual measurement vibration value, and an abnormality diagnosis unit comparing the differential value calculated by the differential value calculating unit and a previously set diagnosis threshold, and diagnosing abnormality of each of the abnormality diagnosis targets based on a result of the comparison.

Also, a bearing according to the second aspect of the present invention is provided with the abnormality diagnosis device according to the foregoing first aspect.

Further, a rotation device according to the third aspect of the present invention is provided with the abnormality diagnosis device according to the foregoing first aspect.

Further, an industrial machine according to the fourth aspect of the present invention is provided with an abnormality diagnosis device according to the foregoing first aspect.

Furthermore, a vehicle according to the fifth aspect of the present invention is provided with the abnormality diagnosis device according to the foregoing first aspect.

Advantageous Effects of Invention

According to the present invention, the diagnosis threshold is compared to the differential value (in short, a change amount from the initial value) between the initial frequency component, which is extracted from the initial vibration value measured at the initial measurement timing, and the actual measurement frequency component, which is extracted from the actual measurement vibration value measured at the actual measurement timing, and it is possible to carry out abnormality diagnosis based on the comparison result. This makes it possible to carry out abnormality diagnosis while the rotation device is operating, and an effect is thus obtained that it is possible to discover abnormality at an early stage. In addition, as compared to before, it is possible to ignore variation of initial values caused by individual differences, and it is thus possible to set diagnosis thresholds without considering variation due to individual differences (by focusing only on change amounts). As a result, an effect is obtained that it is possible to set the diagnosis thresholds more easily as compared to before. Further, although the actual measurement vibration value is an aggregation of variation of the initial values caused by individual differences and variation of the change amounts, there is an effect that, since variation of initial values can be removed by calculating the differences, it is possible to improve measurement reliability accordingly.

DESCRIPTION OF EMBODIMENTS

Figure 1A:
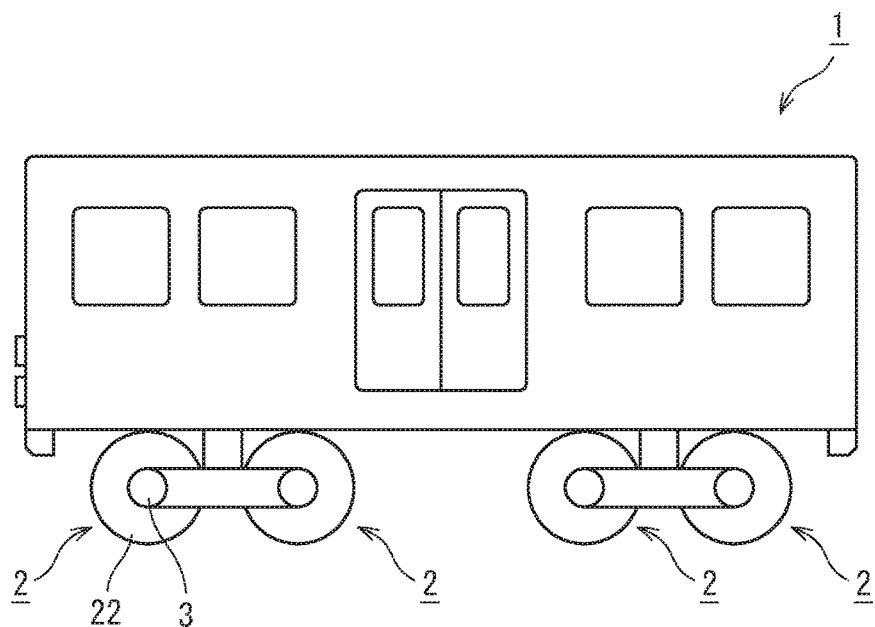
FIGS. 1A and 1B are schematic views illustrating a rough configuration of a railway vehicle 1.

Next, embodiments of the present invention will now be described with reference to the drawings. In description of the following drawings, the same or similar reference numerals are used to the same or similar parts. However, it should be noted that the drawings are schematic, and vertical and lateral dimensions and reduced scales of members or parts are different from actual ones. Therefore, specific dimensions and reduced scales should be determined by considering the explanation below. Therefore, it is obvious that the drawings include parts where dimensional relationships and ratios are mutually different from one another.

Further, the embodiments illustrated below explain examples of a device and a method for embodying the technical ideas of the present invention, and the technical ideas of the present invention do not specify materials, shapes, structures, arrangements and so on of constituents to those stated below. Various changes may be added to the technical ideas of the present invention within a technical range defined by the claims described in the scope of claims.

Embodiments

Configuration

Figure 1B:
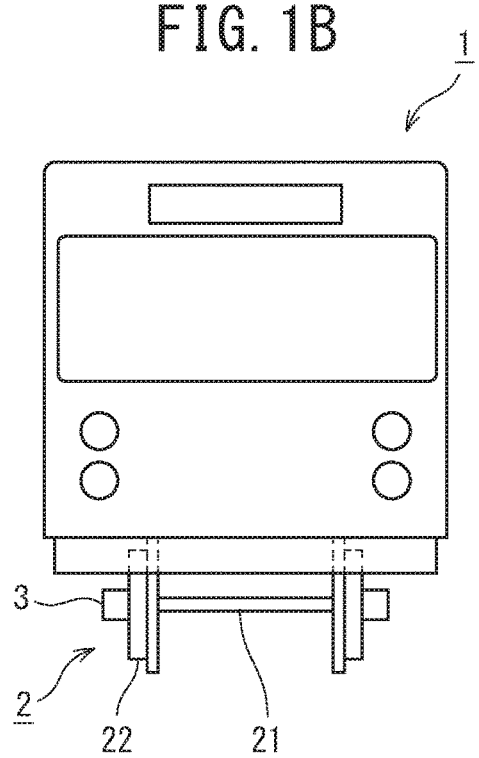

As illustrated in FIGS. 1A and 1B, a railway vehicle 1 according to an embodiment of the present invention is configured by including a plurality of rotation devices 2.

The rotation devices 2 include an axle 21 serving as a rotation shaft, a pair of double row tapered roller bearings 3 that supports the axle 21 in both end parts of the axle 21, and a pair of wheels 22 that is attached to both end parts of the axle 21 on an inner side of the pair of double row tapered roller bearings 3, and serves as rotors.

Figure 2:
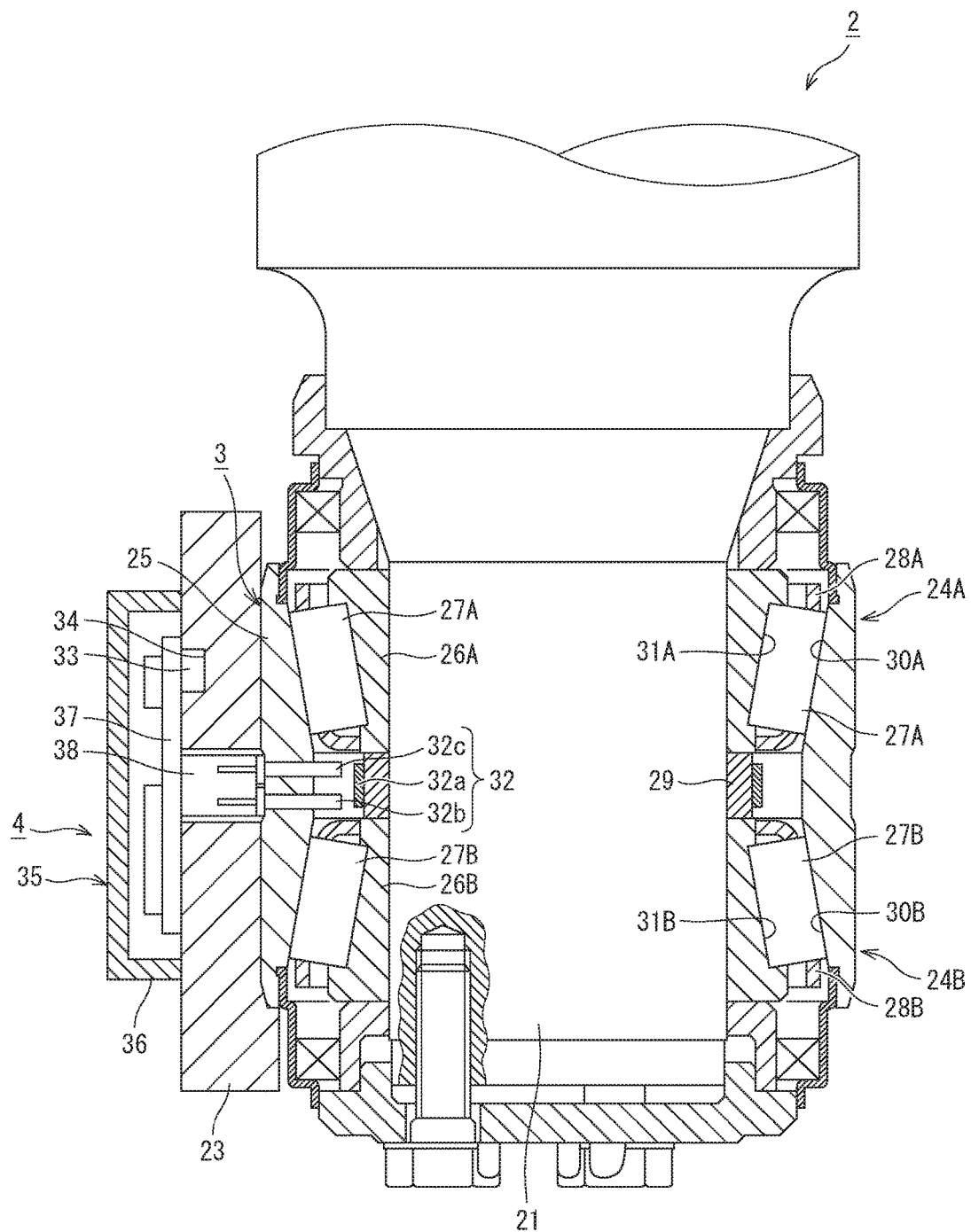
FIG. 2 is a schematic view illustrating a detailed configuration of a main part of a rotation device 2.

As illustrated in FIG. 2, the double row tapered roller bearing 3 supports an end part of the axle 21 on an inner side of a bearing housing 23 so that the axle 21 is able to rotate freely.

The double row tapered roller bearing 3 includes a first tapered roller bearing part 24A, a second tapered roller bearing part 24B, an outer ring 25, and a cylindrical spacer 29.

The first tapered roller bearing part 24A includes a first inner ring 26A, a plurality of first tapered rollers 27A, and a first cage 28A, and the second tapered roller bearing part 24B includes a second inner ring 26B, a plurality of second tapered rollers 27B, and a second cage 28B.

The outer ring 25 is an outer ring common to the first tapered roller bearing part 24A and the second tapered roller bearing part 24B, has a first outer ring raceway 30A and a second outer ring raceway 30B having a double row tapered recessed surface shape on its inner peripheral surface, and is configured to be fitted into the bearing housing 23 so as not to rotate when used.

The first inner ring 26A has a tapered projecting surface-shaped first inner ring raceway 31A on its outer peripheral surface, and the second inner ring 26B has a tapered projecting surface-shaped second inner ring raceway 31B on its outer peripheral surface. The first inner ring 26A and the second inner ring 26B are configured to be fitted and fixed onto the end part of the axle 21 so as to rotate together with the axle 21 when used.

The plurality of first tapered rollers 27A is provided between the first outer ring raceway 30A and the first inner ring raceway 31A, respectively, so as to roll freely in a state of being held by the first cage 28A.

Further, the plurality of second tapered rollers 27B is provided between the second outer ring raceway 30B and the second inner ring raceway 31B, respectively, so as to roll freely in a state of being held by the second cage 28B.

The spacer 29 is fitted onto the end part of the axle 21 in a state of being sandwiched between the first inner ring 26A and the second inner ring 26B. As illustrated in FIGS. 1A and 1B, the wheels 22 are fixed and fitted onto parts close to both ends of an intermediate part of the axle 21, the parts being present above those parts illustrated in FIG. 2.

Further, as illustrated in FIG. 2, the double row tapered roller bearing 3 is configured by including an abnormality diagnosis device 4 that is attached to an outer peripheral surface of the bearing housing 23. This abnormality diagnosis device 4 diagnoses abnormality happening in the constituents of the rotation device 2 that are abnormality diagnosis targets, such as flaws and peeling of the double row tapered roller bearing 3, uneven wear of the axle 21, and flat wear of the wheels 22.

In this embodiment, the abnormality diagnosis target represents not only each constituent, but also a set of one abnormality diagnosis target and each abnormality content in a case where there are two types of abnormality or more happening in each constituent. For example, in the case of wheel flat of the wheel 22, wear at one location per round and wear at two locations per round have different feature frequency components, and, in this case, there are two abnormality diagnosis targets, which are wheel flat (one location) of the wheel 22 and wheel flats (two locations) of the wheel 22.

The abnormality diagnosis device 4 is configured by including a shaft speed sensor 32 serving as a rotation speed detecting unit that detects rotation speed of the axle 21, an acceleration sensor 33 serving as a vibration detecting unit that detects vibration generated in the rotation device 2, and an abnormality diagnosis unit 35 that diagnoses abnormality of the rotation device 2.

The shaft speed sensor 32 is configured by including an encoder 32a configured into a cylindrical shape by using permanent magnet, a first sensor 32b, and a second sensor 32c.

The encoder 32a is fitted and fixed onto an intermediate part of the spacer 29 in an axis direction.

The first sensor 32b and the second sensor 32c are provided in an intermediate part of the outer ring 25 in the axis direction between the first tapered roller 27A and the second tapered roller 27B arranged in double rows, in a state where detecting units of the first sensor 32b and the second sensor 32c are close to and face an outer peripheral surface of the encoder 32a that is a detected surface. On the outer peripheral surface of the encoder 32a, a magnetic pole magnetized with the n-pole and a magnetic pole magnetized with the s-pole are arranged alternately and at equal intervals in the circumferential direction.

Moreover, in the detection parts of the first sensor 32b and the second sensor 32c, magnetic detection elements such as a hall IC, a hall element, MR, and GMR are incorporated. Positions where the detecting units of the first sensor 32b and the second sensor 32c face the outer peripheral surface of the encoder 32a are the same with respect to the circumferential direction of the encoder 32a.

In this embodiment, the acceleration sensor 33 outputs vibration generated near the double row tapered roller bearing 3 as an electric signal.

In this embodiment, as shown in FIG. 2, a recessed part 34 is formed in a part of the outer peripheral surface of the bearing housing 23 in a circumferential direction, corresponding to a center part of the first tapered roller bearing part 24A with respect to the axis direction. Then, the acceleration sensor 33 is housed in the recessed part 34. The position where the acceleration sensor 33 is arranged is not limited to this position, and may be changed to a different position depending on the abnormality diagnosis target and so on.

As the acceleration sensor 33, one that is able to measure acceleration speed in one axis direction, one that is able to measure acceleration speed in two axis directions, one that is able to measure acceleration speed in three axis directions, or the like is selected as appropriate and used depending on vibration characteristics when abnormality happens in the abnormality diagnosis target. Also, such a configuration may be used where a plurality of sensors in one axis or two axes is arranged to meet directions of vibration to be measured. Also, in this embodiment, in a case where abnormality of the abnormality diagnosis target generates vibration in a plurality of axis directions, a vibration direction at the largest vibration level is decided as a representative axis direction among the vibration directions at the time of occurrence of abnormality, and an acceleration sensor that is able to measure vibration in that axis direction is used.

This means that, when, for example, bearing peeling happens in a bearing, since vibration in a radial direction becomes large, it is necessary to arrange a sensor that is able to detect vibration in the radial direction in order to diagnose abnormality of bearing peeling. As stated above, because remarkable vibration changes are observed in different directions depending on abnormality contents, it is necessary to arrange a sensor that is able to detect vibration in a desired vibration direction depending on abnormality content of the diagnosis target.

The present invention is not limited to this configuration, and a configuration that detects two vibrations or more in a plurality of axis directions may be used. In this case, in the abnormality diagnosis processing described later, abnormality diagnosis is carried out for one abnormality diagnosis target based on, for example, a result of comparison between a diagnosis threshold and a differential value between two feature frequency components or more.

The abnormality diagnosis unit 35 includes a substrate housing 36 fixed to the outer peripheral surface of the bearing housing 23, a circuit board 37 arranged on an inner side of the substrate housing 36, and a connector 38 that electrically connects the circuit board 37 and output terminals of the first sensor 32b and the second sensor 32c.

This abnormality diagnosis unit 35 diagnoses whether or not abnormality such as wear and damage is happening in each part that constitutes the rotation device 2, and performs calculation processing of an electric signals and so on output from the shaft speed sensor 32 and the acceleration sensor 33 in order to specify a part where the abnormality is happening.

Figure 3:
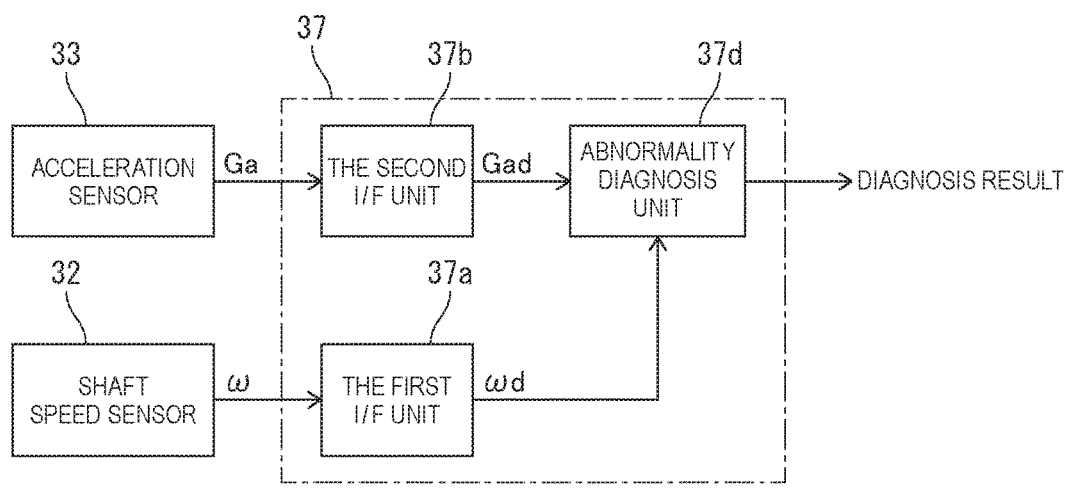
FIG. 3 is a block diagram illustrating a configuration example of an abnormality diagnosis device 4.

Specifically, as illustrated in FIG. 3, the circuit board 37 is configured by including a first I/F part 37a, a second I/F part 37b, and an abnormality diagnosis unit 37d, which are implemented as chip components, discrete components and so on.

The first I/F part 37a convers a rotation speed signal ω, which is an analog electric signal output from the shaft speed sensor 32 and indicating rotation speed of the axle 21, into a signal format with which the later-described abnormality diagnosis unit 37d is able to perform calculation processing.

Here, in this embodiment, the abnormality diagnosis unit 37d is made from a microcomputer on which a CPU (central processing unit) and so on are mounted.

Therefore, although not illustrated, the first I/F part 37a in this embodiment is configured by including, for example, an A/D converter for converting an analog signal into a digital signal, a filter circuit for cutting out a specific frequency band, a capacitor for AC coupling, a signal amplifier for amplifying a signal, and so on.

The first I/F part 37a outputs a converted digital rotation speed signal ωd to the abnormality diagnosis unit 37d.

The second I/F part 37b has similar configuration to that of the first I/F part 37a, and converts an acceleration speed signal Ga, which is an analog electric signal output from the acceleration sensor 33, into a signal format with which the later-described abnormality diagnosis unit 37d is able to perform calculation processing. The second I/F part 37b outputs a converted digital acceleration speed signal Gad to the abnormality diagnosis unit 37d.

In this embodiment, the abnormality diagnosis unit 37d diagnoses whether or not abnormality such as wear and damage is happening in the double row tapered roller bearing 3, the axle 21, and the wheel 22 based on the rotation speed signal ωd from the first I/F part 37a and the acceleration speed signal Gad from the second I/F part 37b.

Figure 4:
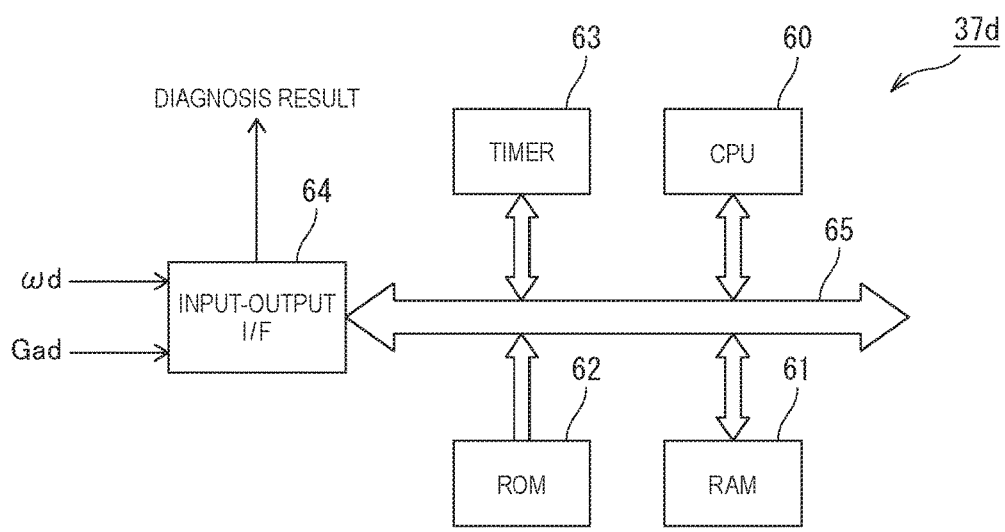
FIG. 4 is a block diagram illustrating an example of a hardware configuration of an abnormality diagnosis unit 37d.
Figure 5:
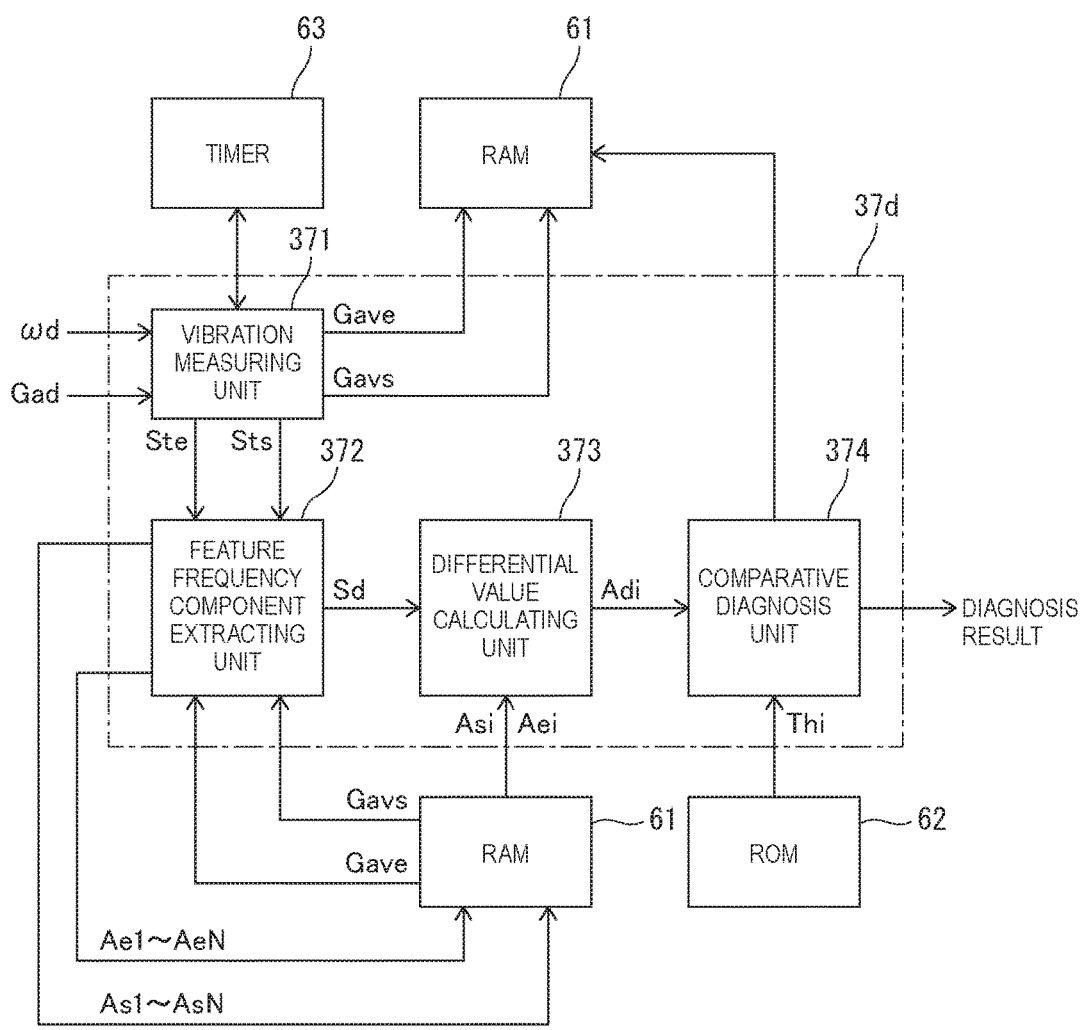
FIG. 5 is a block diagram illustrating an example of a functional configuration of the abnormality diagnosis unit 37d.

Next, based on FIG. 4 and FIG. 5, a hardware configuration and a functional configuration of the abnormality diagnosis unit 37d are explained.

As illustrated in FIG. 4, the abnormality diagnosis unit 37d includes a CPU 60, which is a central processing unit in charge of various types of control and calculation processing, a RAM (random access memory) 61 configuring a main storage, a ROM (read only memory) 62 that is a read-only storage, and a timer 63 for time measurement. In addition, various internal/external buses 65 for data transfer and an input-output interface (I/F) 64 are provided. In this embodiment, the RAM 61 is made of, for example, a nonvolatile memory such as a NOR type flash memory.

Then, the various internal/external buses 65 connect the CPU 60, the RAM 61, the ROM 62, and the timer 63, and the first I/F part 37a and the second I/F part 37b of the abnormality diagnosis unit 35 are connected with the buses 65 through the input-output I/F 64. Other than these, although illustration is omitted, for example, an external storage for securing a data storage capacity, a communication apparatus for transmitting an abnormality diagnosis result through an onboard network to a control device (herein below, referred to as "an integrated control device")

that integrally controls each abnormality diagnosis device and so on, are connected as necessary.

Then, when power is supplied, various computer programs stored in the ROM 62 in advance are loaded on the RAM 61 by a system program such as BIOS stored in the ROM 62 or the like, and, in accordance with instructions described in the programs loaded on the RAM 61, the CPU 60 performs given control and calculation processing by making full use of various resources, thereby realizing later-described each function on a software.

Further, as illustrated in FIG. 5, the abnormality diagnosis unit 37d includes a vibration measuring unit 371, a feature frequency component extracting part 372, a differential value calculating unit 373, and a comparative diagnosis unit 374, as function parts that are realized as the CPU 60 executes programs.

Based on the rotation speed signal $\omega d$ from the first I/F part 37a, the vibration measuring unit 371 measures an acceleration speed value in accordance with vibration generated in the rotation device 2 when the axle 21 is rotating at a previously-set setting rotation speed $\omega s$ at previously set measurement timing.

This means that, when it is determined that the axle 21 is rotating at the setting rotation speed $\omega s$, an acceleration speed value (herein below, referred to as an "acceleration speed value Gav"), which is indicated by the acceleration speed signal Gad input from the second I/F part 37b in a previously-set sampling period, is stored in the RAM 61 in time series. By doing this, vibration generated in the rotation device 2 is measured.

In this embodiment, the vibration measuring unit 371 measures the acceleration speed value Gav in accordance with vibration generated in the rotation device 2 when the axle 21 is rotating at the previously-set setting rotation speed $\omega s$, at previously-set initial measurement timing while rotation device 2 is in operation. In addition, the vibration measuring unit 371 measures the acceleration speed value Gav in accordance with vibration generated in the rotation device 2 when the axle 21 is rotating at the setting rotation speed $\omega s$, at actual measurement timing that is the initial measurement timing or later while the rotation device 2 is in operation.

Further, vibration measuring unit 371 in this embodiment first determines that the axle 21 has started rotating at the setting rotation speed $\omega s$, and then, by using the timer 63, measures elapsed time Tp of a period of time in which rotation at the setting rotation speed $\omega s$ continues. Then, when the elapsed time Tp becomes previously-set diagnosable time Td or longer at the initial measurement timing, the measurement processing is stopped, and an initial extraction start command Ste for commanding start of extraction processing for initial frequency components Ae1~AeN is output to the feature frequency component extracting part 372.

Herein below, the acceleration speed values Gav, which are stored in the RAM 61 until the elapsed time Tp becomes the diagnosable time Td or longer at the initial measurement timing and the measurement is stopped, are referred to as an "initial vibration value group Gave".

Meanwhile, when the elapsed time Tp becomes the diagnosable time Td or longer at the actual measurement timing, the vibration measuring unit 371 stops the measurement processing, and also outputs an actual measurement extraction start command Sts, which commands start of extraction processing for actual measurement frequency components As1~AsN, to the feature frequency component extracting part 372.

Herein below, acceleration speed values Gav, which are stored in the RAM 61 until the elapsed time Tp becomes the diagnosable time Td or longer at the actual measurement timing and the measurement is stopped, are referred to as an "actual measurement vibration value group Gavs".

Further, when the elapsed time Tp is shorter than the diagnosable time Td, regardless of the measurement timing, the vibration measuring unit 371 clears the timer 63 and deletes the acceleration speed values Gav stored so far from the RAM 61. Further, when the extraction processing for the feature frequency components is completed, the feature frequency component extracting part 372 also deletes the acceleration speed values Gav (the initial vibration value group Gave or the actual measurement vibration value group Gavs) corresponding to the completed feature frequency component from the RAM 61.

The vibration measuring unit 371 in this embodiment is configured to perform measurement of the actual measurement vibration value group Gavs every time rotation speed of the axle 21 changes to the setting rotation speed $\omega s$ from other rotation speed at the actual measurement timing.

In accordance to an input of the initial extraction start command Ste from the vibration measuring unit 371, the feature frequency component extracting part 372 performs order analysis processing with respect to the initial vibration value group Gave stored in the RAM 61 at the initial measurement timing. Thus, feature frequency components (herein below, referred to as "initial frequency components Ae1~AeN") are extracted corresponding to previously-set orders 1~N (N is a natural number of 2 or larger) of a measuring target, respectively, which are included in a vibration waveform indicated by the initial vibration value group Gave. The feature frequency component extracting part 372 causes the RAM 61 to store the extracted initial frequency components Ae1~AeN. In this embodiment, since the RAM 61 is made of a nonvolatile memory, the stored initial frequency components Ae1~AeN are saved even after a power source is turned off unless deleted intentionally. Then, in this embodiment, after the initial frequency components Ae1~AeN are extracted once, those stored and saved in the RAM 61 are used repeatedly until a condition for generating the initial measurement timing again is satisfied such as an replacement of a part of the rotation device 2.

Here, it is possible to set the initial measurement timing arbitrarily depending on a previously-set measurement condition, such as the first operation timing after the rotation device 2 is newly introduced, the first operation timing after the rotation device 2 or the bearing is replaced, and the first operation timing after "running-in" when an influence of initial wear needs to be excluded.

Further, the actual measurement timing basically comes at the initial measurement timing or later, and is also operation timing after extraction of the initial frequency components.

Meanwhile, in accordance with an input of the actual measurement extraction start command Sts from the vibration measuring unit 371, the feature frequency component extracting part 372 carries out order analysis processing with respect to the actual measurement vibration value group Gavs stored in the RAM 61 at the actual measurement timing. Thus, feature frequency components (herein below, referred to as "actual measurement frequency components As1~AsN") are extracted corresponding to the orders 1~N, respectively, which are included in a vibration waveform indicated by the actual measurement vibration value group Gavs. The feature frequency component extracting part 372 causes the RAM 61 to store the extracted actual measurement frequency components As1~AsN, and thereafter, outputs a diagnosis start command Sd to the differential value calculating unit 373.

Here, specifically, the order analysis processing obtains a power spectrum (vibration level) of the vibration waveform (the initial vibration value group Gave or the actual measurement vibration value group Gavs) by using a FFT (fast Fourie transform), and obtains a component corresponding to frequency fs that is equivalent to rotation speed (setting rotation speed ωs) when this power spectrum is obtained, as the first component. In addition, the processing obtains power spectrums for the respective frequencies that are twice, three times . . . N−1 times, and N times of the frequency fs, as the second to N-th components. Note that the previously obtained frequency fs equivalent to the setting rotation speed ωs is stored in the RAM 61 or the ROM 62 in advance. Further, the value of N is set as appropriate depending on an order component corresponding to an abnormality diagnosis target.

When the diagnosis start command Sd is input from the feature frequency component extracting part 372, the differential value calculating unit 373 calculates differential values (herein below, referred to as "differential values Ad1~AdN") for the respective orders between the actual measurement frequency components As1~AsN stored in the RAM 61 and the initial frequency components Ae1~AeN stored in the RAM 61 in accordance with the expression (1) below. This means that change amounts until the present time for the respective order components from the initial frequency components Ae1~AeN are calculated.

$$Adi = Asi - Aei \qquad (1)$$

The differential value calculating unit 373 outputs the calculated differential values Ad1~AdN to the comparative diagnosis unit 374.

When the differential values Ad1~AdN are input from the differential value calculating unit 373, the comparative diagnosis unit 374 compares the input differential values Ad1~AdN to diagnosis thresholds Th1~ThN that are previously set for the respective orders. Then, the comparative diagnosis unit 374 diagnoses whether or not abnormality is happening in each of the constituents of the rotation device 2 based on each of the comparison results. The comparative diagnosis unit 374 outputs this abnormality diagnosis result as the first abnormality diagnosis result to, for example, the integrated control device through the onboard network.

Here, depending on parts and devices, a failure mode for each of the order components is decided, such as bearing peeling in a case of the m-th change (m is a natural number of "$1 \leq m < N$"), and device rotation shaft uneven wear in a case of the (m+1)-th change. For example, when the wheel 22 is worn due to some reasons, feature frequency components are generated in such a way that the first component is generated in a case corresponding to wear at one location per round such as wheel flat, and the second component is generated in a case corresponding to wear at two locations such as wear happening in an elliptic shape. Therefore, with regard to the diagnosis thresholds Th1~ThN, a tolerance is considered in each of failure modes to be avoided, and appropriate values are set for the respective order components.

Abnormality Diagnosis Processing

Figure 6:
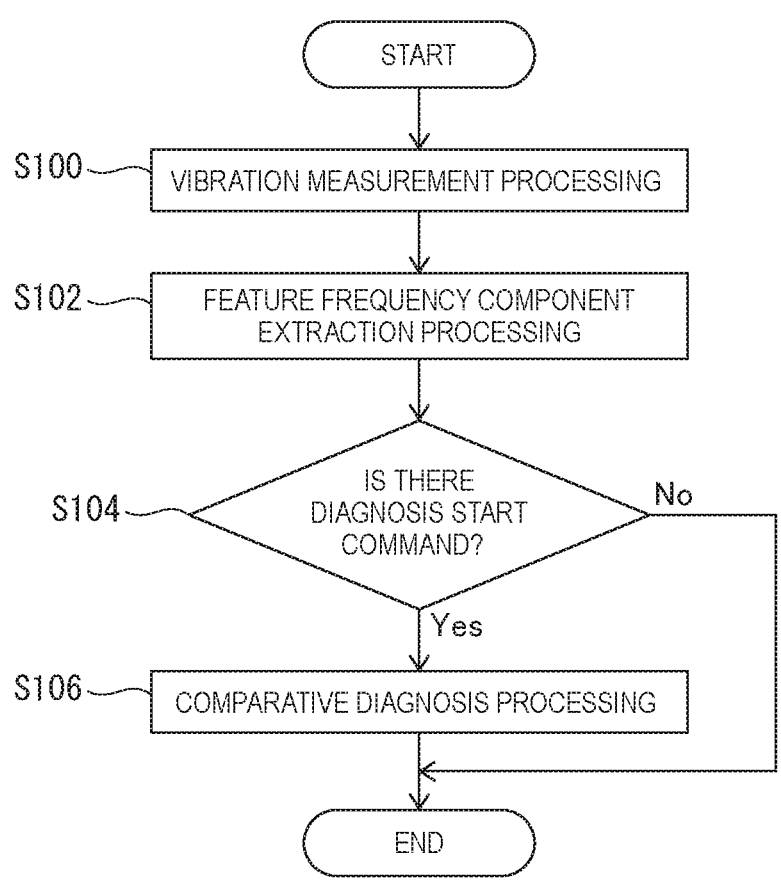
FIG. 6 is a flowchart illustrating an example of processing steps of abnormality diagnosis processing.

Next, based on FIG. 6, an example of processing steps of abnormality diagnosis processing in the abnormality diagnosis device 4 is explained. Note that the abnormality diagnosis processing is processing executed repeatedly at given period while the railway vehicle 1 is operating (while a driving source is driving or a vehicle is running).

Once a program is executed and the abnormality diagnosis processing starts in the CPU 60, the processing first moves to step S100 as illustrated in FIG. 6.

In step S100, the vibration measuring unit 371 carries out vibration measurement processing and measures the initial vibration value group Gave or the actual measurement vibration value group Gavs, and the processing moves on to step S102.

In step S102, the feature frequency component extracting part 372 carries out the feature frequency component extraction processing and extracts the initial frequency components Ae1~AeN or the actual measurement frequency components As1~AsN from the initial vibration value group Gave or the actual measurement vibration value group Gavs, and the processing moves on to step S104.

In step S104, the differential value calculating unit 373 determines whether or not the diagnosis start command Sd is input from the feature frequency component extracting part 372. Then, when it is determined that it is input (Yes), the processing moves to step S106, and, when it is determined otherwise (No), the series of processing ends.

When the processing moves to the step S106, the differential value calculating unit 373 and the comparative diagnosis unit 374 carry out the comparative diagnosis processing and diagnose whether or not abnormality is happening in each of the constituents of the rotation device 2, and the series of processing ends.

Vibration Measurement Processing

Figure 7:
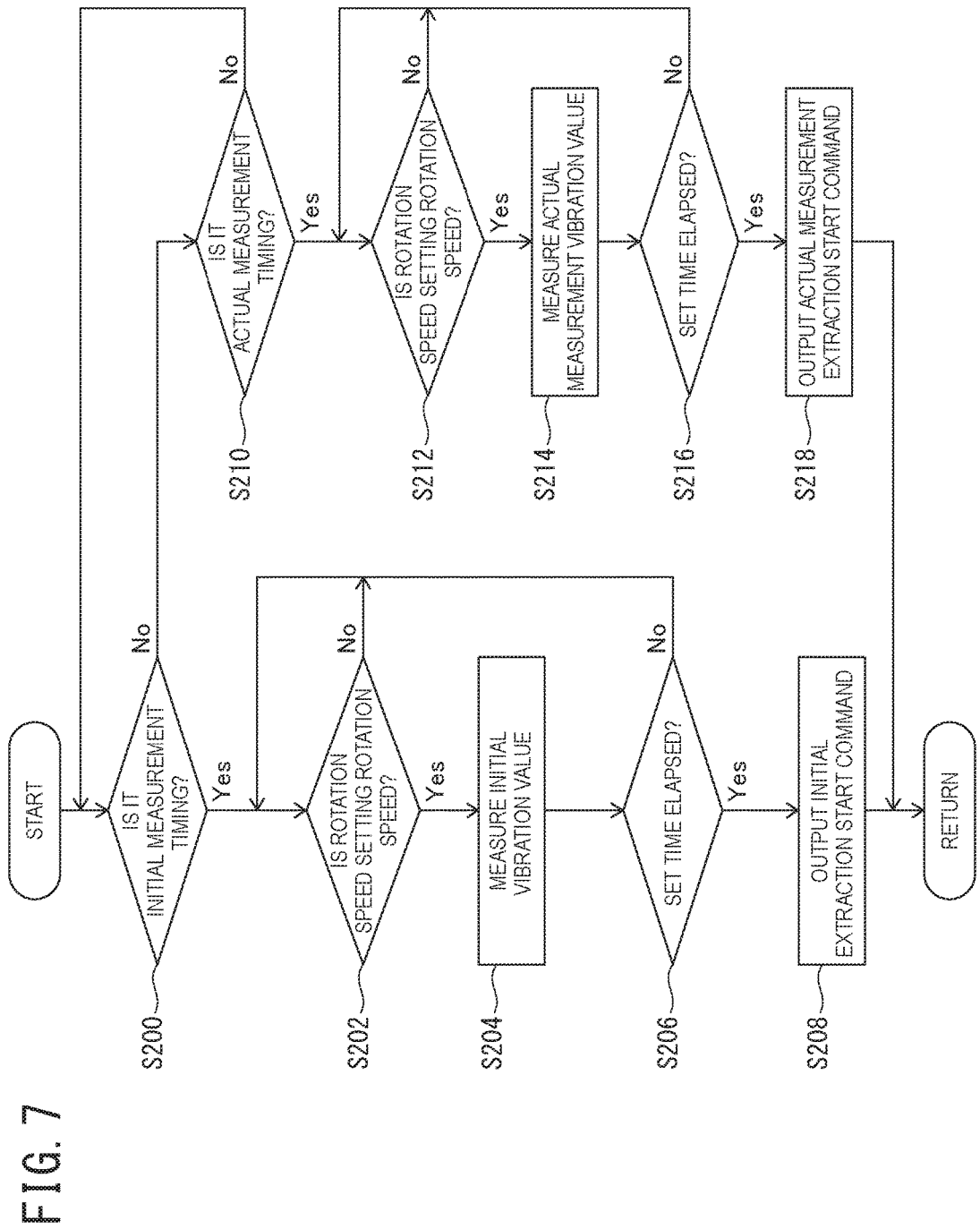
FIG. 7 is a flowchart illustrating an example of processing steps of vibration measurement processing.

Next, based on FIG. 7, an example of processing steps of the vibration measurement processing in step S100 is explained.

Once the vibration measurement processing starts in step S100, the processing first moves to step S200 as illustrated in FIG. 7.

In step S200, the vibration measuring unit 371 determines whether or not the present time is the initial measurement timing, and, when it is determined that the present time is the initial measurement timing (Yes), the processing moves to step S202, and when it is determined otherwise (No), the processing moves to step S210.

Specifically, it is determined whether or not the initial frequency components are stored in the RAM 61, and, when they are not stored, it is determined that it is the initial measurement timing. Note that, in a case where one wants to obtain initial frequency components after running-in at the time of, for example, the first operation of a brand-new device, it is determined whether or not the running-in is happening. When it is determined that the running-in is happening, it is determined that it is not the initial measurement timing.

In the case where the processing moves to the step S202, the vibration measuring unit 371 determines whether or not current rotation speed of the axle 21 is the setting rotation speed ωs, based on the rotation speed signal ωd from the first I/F part 37a. Then, when it is determined that the current rotation speed is the setting rotation speed ωs (Yes), counting of the elapsed time Tp by the timer 63 is started or continued, and the processing moves to step S204, and, when it is determined otherwise (No), the determination processing is repeated until the current rotation speed becomes the setting rotation speed ωs.

Here, when it is first determined that the current rotation speed is the setting rotation speed ωs, measurement (counting) of the elapsed time Tp by the timer 63 begins.

When the processing moves to the step S204, the vibration measuring unit 371 obtains the acceleration speed value Gav based on the acceleration speed signal Gad from the second I/F part 37b, and the obtained acceleration speed value Gav is stored in a previously-set storage area for the initial vibration value group Gave in the RAM 61. Thereafter, the processing moves to step S206.

This means that the vibration measuring unit 371 causes the RAM 61 to store the acceleration speed value Gav obtained at the initial measurement timing as an initial vibration value.

In step S206, the vibration measuring unit 371 determines whether or not the elapsed time Tp has reached the diagnosable time Td or longer based on the value counted by the timer 63, thereby determining whether or not the diagnosable time Td has elapsed since the start of measurement of the initial vibration value. Then, when it is determined that the diagnosable time Td has elapsed (Yes), the measurement ends, the processing moves to step S208, and, when it is determined otherwise (No), the processing moves to step S202.

In a case where the processing moves to step S208, the vibration measuring unit 371 outputs the initial extraction start command Ste to the feature frequency component extracting part 372, the series of processing ends and returns to the initial processing.

Meanwhile, in step S200, when it is not the initial measurement timing and the processing moves to step S210, the vibration measuring unit 371 determines whether or not the present time is the actual measurement timing. Then, when it is determined that the present time is the actual measurement timing (Yes), the processing moves to step S212, and, when it is determined otherwise (No), the processing moves to step S200.

In the case where processing moves to step S212, the vibration measuring unit 371 determines whether or not current rotation speed of the axle 21 is the setting rotation speed ωs. Then, when it is determined that the current rotation speed is the setting rotation speed ωs (Yes), counting of the elapsed time Tp by the timer 63 starts or continues, the processing moves to step S214, and, when it is determined otherwise (No), determination processing is repeated until the current rotation speed becomes the setting rotation speed ωs.

When the processing moves to step S214, the vibration measuring unit 371 obtains the acceleration speed value Gav based on the acceleration speed signal Gad from the second I/F part 37b, and the obtained acceleration speed value Gav is stored in a storage area for the actual measurement vibration value group Gavs in the RAM 61. Thereafter, the processing moves to step S216.

This means that the vibration measuring unit 371 causes the RAM 61 to store the acceleration speed value Gav obtained at the actual measurement timing as an actual measurement vibration value.

In step S216, the vibration measuring unit 371 determines whether or not the elapsed time Tp has reached the diagnosable time Td or longer based on a value counted by the timer 63, thereby determining whether or not the diagnosable time Td has elapsed since the start of measurement of the actual measurement vibration value. Then, when it is determined that the diagnosable time Td has elapsed (Yes), the measurement ends, and the processing moves to step S218, and, when it is determined otherwise (No), the processing moves to step S212.

In the case where the processing moves to step S218, the vibration measuring unit 371 outputs the actual measurement extraction start command Sts to the feature frequency component extracting part 372, the series of processing ends and returns to the initial processing.

Feature Frequency Component Extraction Processing

Figure 8:
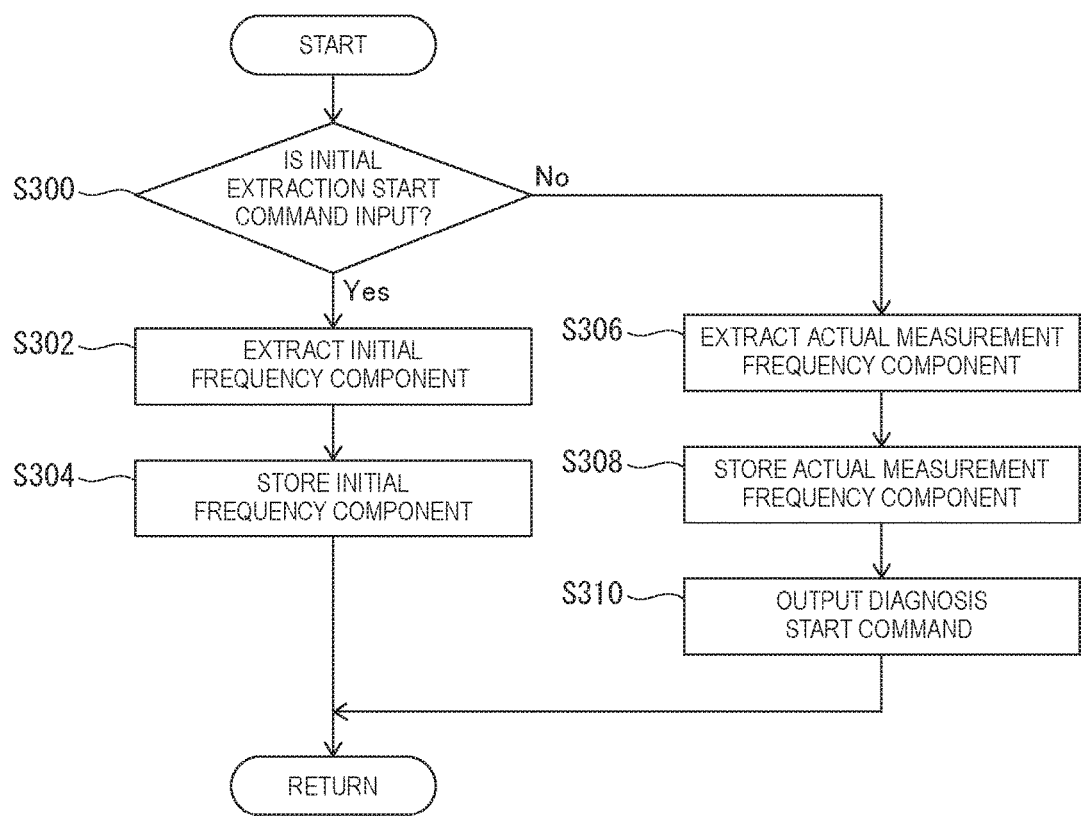
FIG. 8 is a flowchart illustrating an example of processing steps of feature frequency component extraction processing.

Next, based on FIG. 8, an example of processing steps of the feature frequency component extraction processing in step S102 is explained.

Once the feature frequency component extraction processing starts in step S102, the processing first moves to step S300 as illustrated in FIG. 8.

In step S300, the feature frequency component extracting part 372 determines whether or not the initial extraction start command is input from the vibration measuring unit 371. Then, it is determined that the command is input (Yes), the processing moves to step S302, and, when it is determined that actual measurement extraction start command is input (No) on the other hand, the processing moves to step S306.

When the processing moves to step S302, the feature frequency component extracting part 372 carries out the order analysis processing with respect to the initial vibration value group Gave stored in the RAM 61, thereby extracting the initial frequency components Ae1~AeN from the initial vibration value group Gave. Thereafter, the processing moves to step S304.

In step S304, the feature frequency component extracting part 372 causes the RAM 61 to store the initial frequency components Ae1~Ae4 extracted in step S302, and the series of processing ends and returns to the initial processing.

Meanwhile, in step S300, when the actual measurement extraction start command Sts is input and the processing moves to step S306, the feature frequency component extracting part 372 carries out the order analysis processing with respect to the actual measurement vibration value group Gavs stored in the RAM 61, and extracts the actual measurement frequency components As1~AsN from the actual measurement vibration value group Gavs. Thereafter, the processing moves to step S308.

In step S308, the feature frequency component extracting part 372 causes the RAM 61 to store the actual measurement frequency components As1~As4 extracted in step S306, and the processing moves to step S310.

In step S310, the feature frequency component extracting part 372 outputs the diagnosis start command Sd to the differential value calculating unit 373, and the series of processing ends and returns to the initial processing.

Comparative Diagnosis Processing

Figure 9:
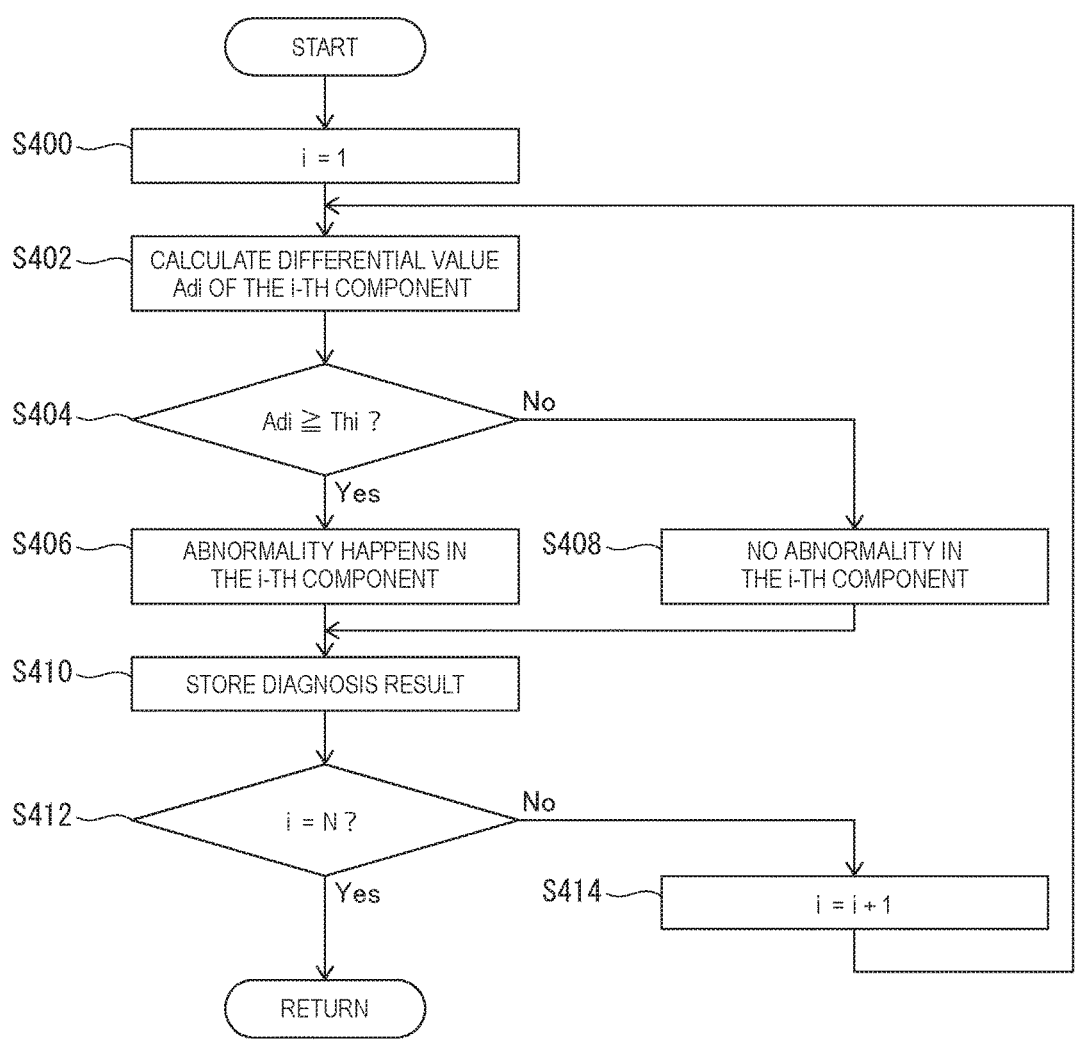
FIG. 9 is a flowchart illustrating an example of processing steps of comparative diagnosis processing.

Next, based on FIG. 9, an example of processing steps of the comparative diagnosis processing in step S106 is explained.

Once the comparative diagnosis processing starts in step S106, the processing first moves to step S400 as illustrated in FIG. 9.

In step S400, the differential value calculating unit 373 substitutes "1" for a variable i, and the processing moves to step S402.

In step S402, the differential value calculating unit 373 reads an initial frequency component Aei and an actual measurement frequency component Asi from the RAM 61, and calculates a differential value Adi of the i-th component in accordance with the foregoing expression (1). Then, the calculated differential value Adi is output to the comparative diagnosis unit 374, and the processing moves to step S404.

Specifically, for example, when the variable i is "1", the differential value calculating unit 373 reads an initial frequency component Ae1 and an actual measurement frequency component As1 from the RAM 61, and calculates "Ad1=As1−Ae1".

In step S404, once the differential value Adi is input to the comparative diagnosis unit 374 from the differential value calculating unit 373, the comparative diagnosis unit 374 reads the diagnosis threshold Thi corresponding to the i-th component from the RAM 61. Then, a large-small comparison is done for the read diagnosis threshold Thi and the input differential value Adi, and, when it is determined that the differential value Adi is the diagnosis threshold Thi or larger (Yes), the processing moves to step S406, and, when it is determined otherwise (No), the processing moves to step S408.

Specifically, for example, when the variable i is "1", the comparative diagnosis unit 374 reads the diagnosis threshold Th1 corresponding to the first component from the RAM 61, and determines whether or not the differential value Ad1 is the diagnosis threshold Th1 or larger. This means that presence of abnormality is diagnosed by determining whether or not the differential value Adi, which is equivalent to an amount of change from the initial value of the i-th component, is the diagnosis threshold Thi or larger.

When the processing moves to the step S406, the comparative diagnosis unit 374 diagnoses that abnormality is happening in a constituent corresponding to the i-th component. Thereafter, the processing moves to step S410.

Meanwhile, when the processing moves to step S408, the comparative diagnosis unit 374 diagnoses that no abnormality is present in the constituent corresponding to the i-th component. Thereafter, the processing moves to step S410.

In step S410, the comparative diagnosis unit 374 causes the RAM 61 to store the diagnosis result in step S406 or S408, and the processing moves to step S412.

In step S412, the comparative diagnosis unit 374 determines whether or not the value of the variable i coincides with N (a set maximum order), and, when it is determined that they coincide with each other (Yes), the series of processing ends and returns to the initial processing, and, when it is determined that they do not coincide with each other (No), the processing moves to step S414.

When the processing moves to step S414, the comparative diagnosis unit 374 substitutes a value, which is obtained by adding 1 to a value of the current variable i, for the variable i, and the processing moves to step S402. This means that, when the value of the current variable i is "1", "1+1=2" is substituted for the variable i.

In this way, the comparative diagnosis processing is carried out for the actual measurement frequency components As1~AsN sequentially, and it is diagnosed whether or not abnormality is happening in a constituent corresponding to each of the actual measurement frequency components (each of the order components).

Note that, this embodiment has a configuration where one acceleration sensor is arranged near one double row tapered roller bearing 3, but, when a double row or four row bearing is included, one acceleration sensor may be arranged near each row of tapered rollers. In this case, two to four diagnosis results are output with regard to the same part. Therefore, for example, the integrated control device may have a configuration where these two to four diagnosis results are displayed on a monitor or the like for a driver's seat, or a comprehensive determination is made whether or not abnormality is present in each part based on the two to four diagnosis results with regard to the same part, and the result is displayed on a monitor or the like for the driver's seat as a diagnosis result.

Operation

Figure 10:
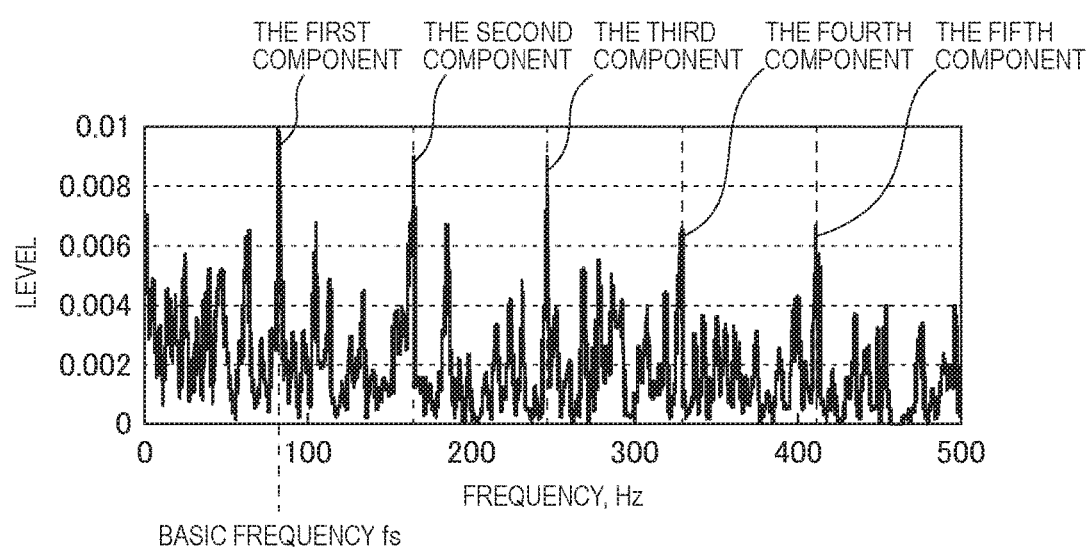
FIG. 10 is a view illustrating an example of a spectrum curve of a vibration waveform.

Next, based on FIG. 10, a specific operation example of the railway vehicle 1 according to this embodiment is explained.

When the railway vehicle 1 starts operating and power source is supplied to various devices including the rotation device 2, the shaft speed sensor 32 starts detection of rotation speed of the axle 21, and the acceleration sensor 33 starts outputting acceleration speed in accordance with vibration generated in the rotation device 2. Then, the analog rotation speed signal $\omega$ output from the shaft speed sensor 32 is input to the abnormality diagnosis unit 37*d* through the first I/F part 37*a* as the digital rotation speed signal $\omega d$.

Meanwhile, the analog acceleration speed signal Ga output from the acceleration sensor 33 is input to the abnormality diagnosis unit 37*d* through the second I/F part 37*b* as the digital acceleration speed signal Gad.

Then, the acceleration speed signal Gad becomes, for example, a signal in which unnecessary frequency components are removed by the filter circuit (low pass filter or bandpass filter) of the second I/F part 37*b*.

Also, in the vibration measuring unit 371, the abnormality diagnosis unit 37*d* determines whether or not the present time is the initial measurement timing. Here, it is assumed that the initial frequency components Ae1~AeN are stored in the RAM 61 already and the vibration measuring unit 371 determines that the present time is not the initial measurement timing. Also, here, it is assumed that N=5 and the initial frequency components Ae1~Ae5 are stored in the RAM 61.

Therefore, the vibration measuring unit 371 determines that the present time is the actual measurement timing, and starts measuring an actual measurement vibration value.

Specifically, the vibration measuring unit 371 determines whether or not rotation speed of the axle 21 has reached the setting rotation speed $\omega s$ based on the rotation speed signal $\omega d$ that is input sequentially at given sampling period. Then, without complete match and within a previously-set error range, it can be determined that the rotation speed has reached the setting rotation speed $\omega s$.

When it is determined that the rotation speed of the axle 21 has reached the setting rotation speed $\omega s$, the vibration measuring unit 371 starts counting by the timer 63, and also causes the RAM 61 to store the acceleration speed values Gvd in time series as actual measurement vibration values based on acceleration speed signals Gad that are sequentially input at given sampling period. Then, when it is determined that the diagnosable time Td has elapsed in a rotation status of the axle 21 at the setting rotation speed $\omega s$, measurement of the actual measurement vibration values ends. Therefore, the RAM 61 stores the actual measurement vibration value group Gavs made of the actual measurement vibration values that are measured in a period until the elapse of the diagnosable time Td. Thereafter, the actual measurement extraction start command Sts is output to the feature frequency component extracting part 372.

In accordance with the actual measurement extraction start command Sts from the vibration measuring unit 371, the feature frequency component extracting part 372 carries out the order analysis processing with respect to the actual measurement vibration value group Gavs stored in the RAM 61, and extracts the actual measurement frequency components As1~As5 that are feature frequency components regarding abnormality happening in each of the constituents of the rotation device 2.

Specifically, with processing such as FFT, the feature frequency component extracting part 372 obtains, for example, a spectrum curve illustrated in FIG. 10 from the actual measurement vibration value group Gavs. Then, as illustrated in FIG. 10, the feature frequency component extracting part 372 extracts a frequency component of basic frequency fs as the first component, and, here, also extracts frequency components that are two to five times of the basic frequency as the second to fifth components in accordance with the initial frequency components Ae1~Ae5. Then, these extracted first to fifth components are stored in the RAM 61 as the actual measurement frequency components As1~As5. Thereafter, the diagnosis start command Sd is output to the differential value calculating unit 373.

In accordance with the diagnosis start command Sd from the feature frequency component extracting part 372, the differential value calculating unit 373 calculates differential values Ad1~Ad5 that are differential values between the actual measurement frequency components As1~As5 stored in the RAM 61, and the initial frequency components Ae1~Ae5 also stored in the RAM 61 in the same orders, respectively.

Then, the calculated differential values Ad1~Ad5 are output sequentially to the comparative diagnosis unit 374.

The comparative diagnosis unit 374 compares the differential values Ad1~Ad5, which are input sequentially from the differential value calculating unit 373, and diagnosis thresholds Th1~Th5 stored in the ROM 62, in the same orders (numbers at the end), respectively, determines that abnormality is happening in a part corresponding to each of the orders with which the differential value is the diagnosis threshold or larger, and determines that no abnormality is happening in a part corresponding to each of the orders with a value smaller than the diagnosis threshold. The comparative diagnosis unit 374 causes the RAM 61 to store this diagnosis result, and also transmits the diagnosis result to, for example, the integrated control device through the onboard network.

Based on the diagnosis result, the integrated control device, for example, causes a monitor for a driver's seat to display information of the diagnosis result regarding presence of abnormality happening in each of the diagnosis target parts of the rotation device 2 that is a target, together with information indicating locations of the rotation device 2 and the constituents. Also, when abnormality happens, depending on content of the abnormality, a message encouraging replacement of a part or a warning message may be displayed, an alarm may be sounded, or a warning lamp may be lit.

Here, the double row tapered roller bearing 3 corresponds to the bearing, the axle 21 corresponds to the rotation shaft, the wheel 22 corresponds to the rotor, the acceleration sensor 33 corresponds to the vibration detecting unit, the shaft speed sensor 32 corresponds to the rotation speed detecting unit, and the comparative diagnosis unit 374 corresponds to the abnormality diagnosis unit.

Effects of the Embodiment (1) In the abnormality diagnosis device 4, the acceleration sensor 33 detects vibration generated in the rotation device 2 configured by including the double row tapered roller bearing 3 that supports the axle 21. The shaft speed sensor 32 detects rotation speed of the axle 21. When the axle 21 is rotating at the setting rotation speed $\omega$s, the vibration measuring unit 371 measures vibration generated in the rotation device 2 based on a detection result of the shaft speed sensor 32 and a detection result of the acceleration sensor 33.

In addition, from the initial vibration values (the initial vibration value group Gave), which are vibration values measured by the vibration measuring unit 371 at the previously set initial measurement timing, the feature frequency component extracting part 372 extracts the feature frequency components (initial frequency components Ae1~AeN) regarding abnormality of abnormality diagnosis targets in the rotation device 2. The feature frequency component extracting part 372 extracts feature frequency components (actual measurement frequency components As1~AsN) of the abnormality diagnosis targets from the actual measurement vibration values (actual measurement vibration value group Gavs), which are vibration values measured by the vibration measuring unit 371 at actual measurement timing that is the previously set initial measurement timing or later.

Further, the differential value calculating unit 373 calculates differential values (differential values Ad1~AdN) between the actual measurement frequency components As1~AsN and the actual measurement frequency components As1~AsN. The comparative diagnosis unit 374 compares the differential values Ad1~AdN calculated by the differential value calculating unit 373 to the previously set diagnosis thresholds Th1~ThN, and diagnoses abnormality in each of the abnormality diagnosis targets based on a result of the comparison.

With this structure, the diagnosis thresholds are compared to the differential values (in short, change amounts from the initial values) between the initial frequency components extracted from the initial vibration values measured at the initial measurement timing while the rotation device 2 is operating, and actual measurement frequency components extracted from the actual measurement vibration values measured at the actual measurement timing while the rotation device 2 is operating, thereby making it possible to carry out abnormality diagnosis based on the comparison result.

Here, in a case where a mechanical damage occurs in a constituent of the rotation device, such as the bearing, vibration and noise increase as the damage inside the part expands, and, in the worst case scenario, a damaged piece could be stuck and possibly lock rotation. Therefore, in order to avoid such a device failure and accident, it is necessary to detect and deal with a damage when it is still small.

With the configuration (1) described above, since the abnormality diagnosis can be done while the rotation device 2 is operating (in short, while the railway vehicle 1 is in operation), an effect is obtained that early discovery of abnormality is possible. In addition, since the abnormality diagnosis is carried out by comparing the diagnosis thresholds to the differential values, it becomes possible to ignore variation in initial values caused by individual differences as compared to before, and it is possible to set diagnosis thresholds without considering variation due to individual differences (by focusing only on change amounts). As a result, an effect is obtained that, it is possible to set the diagnosis thresholds more easily as compared to before.

Further, although the actual measurement vibration value is an aggregation of variation of the initial values caused by individual differences and variation of the change amounts, there is an effect that it is possible to improve measurement reliability for variation of initial values, which can be removed by calculating the differences.

(2) The rotation device 2 is configured by including the double row tapered roller bearing 3, the axle 21, and the wheel 22. The abnormality diagnosis targets for the abnormality diagnosis device 4 are at least the constituents of the rotation device 2 including the double row tapered roller bearing 3, the axle 21, and the wheel 22.

With this configuration, it is possible to diagnose abnormality for each of the constituents of the rotation device 2, thereby making it possible to repair and replace each of the constituents. Because of this, it is possible to reduce cost for maintaining the rotation device.

(3) In the abnormality diagnosis device 4, the feature frequency component extracting part 372 extracts the feature frequency components (initial frequency components Ae1~AeN, the actual measurement frequency components As1~AsN, and second actual measurement frequency components Bs1~BsN) by carrying out the order analysis processing. With this configuration, it is possible to extract feature frequency components regarding abnormality happening in each of the constituents of the rotation device 2 easily and appropriately.

Here, each of the feature frequency components extracted as the order component by the order analysis processing corresponds to content of failure of each of the constituents, such as bearing peeling in a case of the m-th component (m is a natural number of "1≤m<N"), and device rotating shaft uneven wear in a case of the (m+1)-th component.

(4) In the abnormality diagnosis device 4, after the feature frequency component extracting part 372 extracts the initial frequency components, the vibration measuring unit 371 measures an actual measurement vibration value every time rotation speed of the axle 21 reaches the setting rotation speed ωs, the feature frequency component extracting part 372 extracts an actual measurement frequency component from the measured actual measurement vibration value, the differential value calculating unit 373 calculates a differential value between the initial frequency component and the extracted actual measurement frequency component, and the comparative diagnosis unit 374 compares the calculated differential value to the diagnosis threshold and diagnoses abnormality of each of the abnormality diagnosis targets based on a result of the comparison.

With this configuration, after the initial frequency component is extracted, it is possible to automatically execute the series of processing from the measurement of an actual measurement vibration value through the abnormality diagnosis repeatedly every time rotation speed of the axle 21 reaches the setting rotation speed ωs. In the foregoing embodiment, the feature frequency component extraction processing, the differential value calculation processing, and the abnormality diagnosis processing are executed for the actual measurement vibration values measured by the vibration measuring unit 371, every time the axle 21 rotates at the setting rotation speed ωs until the elapse of the diagnosable time Td from start of measurement of an actual measurement vibration value at the time when rotation speed of the axle 21 reaches the setting rotation speed ωs.

Because of this, it is possible to detect abnormality of the abnormality diagnosis targets, which occurs while the rotation device 2 is in operation, at an earlier stage.

(5) In the abnormality diagnosis device 4, when the feature frequency component extracting part 372 determines that the vibration measuring unit 371 has measured vibration for an amount of time of at least the previously set diagnosable time Td at the initial measurement timing, the extraction processing of the initial frequency components (initial frequency components Ae1~AeN) is executed with regard to the initial vibration values (initial vibration value group Gave) for the amount of time of at least the diagnosable time Td. When the feature frequency component extracting part 372 determines that the vibration measuring unit 371 has measured vibration for the amount of time of at least the diagnosable time Td at actual measurement timing, the extraction processing of the actual measurement frequency components (actual measurement frequency components As1~AsN and the second actual measurement frequency components Bs1~BsN) is executed with respect to the actual measurement vibration values (initial vibration value group Gave) for the amount of time of at least the diagnosable time Td.

With this configuration, it is possible to extract initial frequency components from a sufficient number of initial vibration values in order to perform the abnormality diagnosis, and it is thus possible to extract actual measurement frequency components from a sufficient number of actual measurement vibration values in order to carryout the abnormality diagnosis. Because of this, it becomes possible to carry out the abnormality diagnosis based on the feature frequency components appropriate for carrying out the abnormality diagnosis, thereby making it possible to improve reliability of abnormality diagnosis results.

(6) The double row tapered roller bearing 3 includes the abnormality diagnosis device 4.

With this configuration, it is possible to obtain action and effect equivalent to the action and effect of the abnormality diagnosis device 4 described in any one of the foregoing (1)~(5).

(7) The rotation device 2 includes the abnormality diagnosis device 4.

With this configuration, it is possible to obtain action and effect equivalent to the action and effect of the abnormality diagnosis device 4 described in any one of the foregoing (1)~(5).

(8) The railway vehicle 1, which is a kind of an industrial machine, includes the abnormality diagnosis device 4.

With this configuration, it is possible to obtain action and effect equivalent to the action and effect of the abnormality diagnosis device 4 described in any one of the foregoing (1)~(5).

MODIFIED EXAMPLES (1) In the foregoing embodiment, the acceleration sensor is explained as an example of a sensor that detects vibration, but the present invention is not limited to this configuration. For example, another sensor may be used as long as it is able to turn a physical quantity generated because of vibration of the rotation device 2 into an electric signal, such as an AE (acoustic emission) sensor, an ultrasonic wave sensor, a shock pulse sensor, a microphone and so on, or a speed, acceleration speed, distortion, stress, or displacement-type sensor. Also, when attached to a mechanical device with a lot of noise, use of an insulation type is preferred because it is less likely that influence of noise is received. Further, in a case where a vibration detection element such as a piezoelectric device is used, the element may be configured by being molded in plastic or the like.

(2) In the foregoing embodiment, although one acceleration sensor is provided for one double row tapered roller bearing, the present invention is not limited to this configuration, and two acceleration sensors or more may be provided for one double row tapered roller bearing.

(3) In the foregoing embodiment, although the abnormality diagnosis processing is carried out for an acceleration speed signal output by one acceleration sensor, the present invention is not limited to this configuration. For example, two acceleration sensors may be provided, and the abnormality diagnosis unit may carry out the abnormality diagnosis processing for two acceleration speed signals output from the two acceleration sensors. In this case, for example, an average value of two acceleration speed values obtained from the two acceleration speed signals is obtained, and the abnormality diagnosis processing is carried out for the average value.

(4) In the foregoing embodiment, although rotation speed of an axle whose vibration is measured is only one kind, which is the setting rotation speed ωs, the present invention is not limited to this configuration, and a plurality of types of rotation speed may be set. In the case of such a configuration, it is possible to make comprehensive determination about abnormality from diagnosis results from the respective types of rotation speed, thereby making it possible to improve reliability of an abnormality diagnosis result.

(5) In the foregoing embodiment, although the double row tapered roller bearing is explained as an example of the bearing that supports the rotation shaft (axle), the present invention is not limited to this configuration. Other bearings may be used such as other roller bearings including a cylindrical roller bearing, a needle roller bearing, and a self-aligning bearing, and a ball bearing including a deep groove ball bearing, an angular ball bearing. The configuration is not limited to the double-row bearing, and other configuration may be possible, such as a single-row bearing and a four-row bearing.

(6) In the foregoing embodiment, although the axle (rotation shaft), the bearing, the wheel (rotor) are regarded as the abnormality diagnosis targets, the present invention is not limited to this configuration. For example, the configuration may include other constituents such as a gear attached to the axle as an abnormality diagnosis target. For example, when the present invention is applied to a rotation device of a wind mill, a hub, a nasser or the like may be included in the abnormality diagnosis targets, in addition to a blade (rotor), a rotation shaft, and a bearing that structure the rotation device. This means that, in the present invention, anything may be the abnormality diagnosis target as long as it is a constituent that configures a rotation device in which a bearing is incorporated, and is able to perform abnormality diagnosis from feature frequency components included in vibration. Also, on the contrary, the abnormality diagnosis targets may be narrowed down within a range including a bearing, such as a bearing only, a bearing and a wheel only, or a bearing and an axle only.

(7) In the foregoing embodiment, although the present invention is applied to a railway vehicle that is a kind of a vehicle, the present invention is not limited to this configuration, and may be applied to other vehicles such as a four-wheel automobile, a motorcycle, and so on.

(8) In the foregoing embodiment, although the sensor that detects vibration is provided near the double row tapered roller bearing, the present invention is not limited to this configuration, and the sensor may be provided in different positions as long as the sensor is able to detect vibration containing feature frequency components with regard to abnormality of constituents of a rotation device.

(9) In the foregoing embodiment, although the present invention is applied to a railway vehicle that is a kind of an industrial machine, the present invention is not limited to the configuration. The present invention may be applied to any industrial machine as long as it has a rotation device in which a bearing is incorporated, such as mining machinery, chemical machinery, an environmental device, a power transmission device, a tank, a business laundry machine, a boiler and a motor, a plastic machine, pneumatic and hydraulic machinery, a transporting machine, and an iron and steel making machine.

(10) In the foregoing embodiment, although the abnormality diagnosis device is attached to the end surface of the bearing, the present invention is not limited to this configuration. The abnormality diagnosis device may be arranged, for example, in a different environment separated from the bearing depending on usage and environment resistance of the abnormality diagnosis device. In this case, various sensors provided near the bearing are connected so as to be able to communicate through wire or wirelessly.

Further, the present invention is not limited to each of the embodiments described above, and deformations, improvements and so on are included in the present invention within a range where the object of the present invention is achieved.

The content described in Japanese Patent Application P 2014-250033 (filed on Dec. 10, 2014), to which this application claims priority, is hereby incorporated as reference in its entirety.

Here, although explanation is given with reference to the limited number of embodiments, the scope of rights is not limited to them, and alternations of each of the embodiments based on the above disclosure are obvious to a person skilled in the art.

REFERENCE SIGNS LIST

1 RAILWAY VEHICLE
2 ROTATION DEVICE
3 DOUBLE ROW TAPERED ROLLER BEARING
4 ABNORMALITY DIAGNOSIS DEVICE
21 AXLE
22 WHEEL
32 SHAFT SPEED SENSOR
33 ACCELERATION SENSOR
37 CIRCUIT BOARD
37a~37b THE FIRST TO SECOND I/F UNITS
37d ABNORMALITY DIAGNOSIS UNIT
371 VIBRATION MEASURING UNIT
372 FEATURE FREQUENCY COMPONENT EXTRACTING UNIT
373 DIFFERENTIAL VALUE CALCULATING UNIT
374 COMPARATIVE DIAGNOSIS UNIT

The invention claimed is:
1. An abnormality diagnosis device comprising:
a vibration detecting unit detecting vibration generated in a rotation device configured by including a bearing that supports a rotation shaft;
a rotation speed detecting unit detecting rotation speed of the rotation shaft;
a vibration measuring unit measuring vibration generated in the rotation device while the rotation shaft is rotating at previously set setting rotation speed, based on a detection result of the rotation speed detecting unit and a detection result of the vibration detecting unit;
an initial frequency component extraction unit extracting a feature frequency component regarding abnormality of each abnormality diagnosis target of the rotation device, from an initial vibration value, which is a value of the vibration measured by the vibration measuring unit at previously set initial measurement timing while the rotation device is operating;

an actual measurement frequency component extraction unit extracting the feature frequency component from an actual measurement vibration value, which is a value of the vibration measured by the vibration measuring unit at actual measurement timing that is the previously set initial measurement timing or later while the rotation device is operating;

a differential value calculating unit calculating a differential value between an initial frequency component, which is the feature frequency component extracted from the initial vibration value, and an actual measurement frequency component, which is the feature frequency component extracted from the actual measurement vibration value; and an abnormality diagnosis unit comparing the differential value calculated by the differential value calculating unit and a previously set diagnosis threshold, and diagnosing abnormality of each of the abnormality diagnosis targets based on a result of the comparison, wherein after the initial frequency component extraction unit extracts the initial frequency component, the vibration measuring unit measures the actual measurement vibration value every time rotation speed of the rotation shaft becomes the setting rotation speed, the actual measurement frequency component extracting unit extracts the actual measurement frequency component from the measured actual measurement vibration value, the differential value calculating unit calculates a differential value between the initial frequency component and the extracted actual measurement frequency component, and the abnormality diagnosis unit compares the calculated differential value and the diagnosis threshold and diagnoses abnormality of each of the abnormality diagnosis targets based on a result of the comparison.

2. The abnormality diagnosis device according to claim 1, wherein
the rotation device is configured by including the bearing, the rotation shaft, and a rotor supported by the bearing, and
the abnormality diagnosis target is at least a constituent of the rotation device including the bearing, the rotation shaft, and the rotor.

3. The abnormality diagnosis device according to claim 2, wherein
the initial frequency component extraction unit and the actual measurement frequency component extraction unit extract the feature frequency component by order analysis processing.

4. The abnormality diagnosis device according to claim 2, wherein,
when it is determined that the vibration measuring unit has measured the vibration for a period of time of previously set diagnosable time or longer at the initial measurement timing, the initial frequency component extraction unit carries out extraction processing of the initial frequency component with respect to the initial vibration value for the period of time of the diagnosable time or longer, and,
when it is determined that the vibration measuring unit has measured the vibration for a period of time of the diagnosable time or longer at the actual measurement timing, the actual measurement frequency component extraction unit carries out extraction processing of the actual measurement frequency component with respect to the actual measurement vibration value for the period of time of the diagnosable time or longer.

5. The abnormality diagnosis device according to claim 1, wherein
the initial frequency component extraction unit and the actual measurement frequency component extraction unit extract the feature frequency component by order analysis processing.

6. The abnormality diagnosis device according to claim 5, wherein,
when it is determined that the vibration measuring unit has measured the vibration for a period of time of previously set diagnosable time or longer at the initial measurement timing, the initial frequency component extraction unit carries out extraction processing of the initial frequency component with respect to the initial vibration value for the period of time of the diagnosable time or longer, and,
when it is determined that the vibration measuring unit has measured the vibration for a period of time of the diagnosable time or longer at the actual measurement timing, the actual measurement frequency component extraction unit carries out extraction processing of the actual measurement frequency component with respect to the actual measurement vibration value for the period of time of the diagnosable time or longer.

7. The abnormality diagnosis device according to claim 1, wherein,
when it is determined that the vibration measuring unit has measured the vibration for a period of time of previously set diagnosable time or longer at the initial measurement timing, the initial frequency component extraction unit carries out extraction processing of the initial frequency component with respect to the initial vibration value for the period of time of the diagnosable time or longer, and,
when it is determined that the vibration measuring unit has measured the vibration for a period of time of the diagnosable time or longer at the actual measurement timing, the actual measurement frequency component extraction unit carries out extraction processing of the actual measurement frequency component with respect to the actual measurement vibration value for the period of time of the diagnosable time or longer.

8. A bearing, comprising:
an abnormality diagnosis device, wherein the abnormality diagnosis device comprises:
a vibration detecting unit detecting vibration generated in a rotation device configured by including the bearing that supports a rotation shaft;
a rotation speed detecting unit detecting rotation speed of the rotation shaft;
a vibration measuring unit measuring vibration generated in the rotation device while the rotation shaft is rotating at previously set setting rotation speed, based on a detection result of the rotation speed detecting unit and a detection result of the vibration detecting unit;
an initial frequency component extraction unit extracting a feature frequency component regarding abnormality of each abnormality diagnosis target of the rotation device, from an initial vibration value, which is a value of the vibration measured by the vibration measuring unit at previously set initial measurement timing while the rotation device is operating;
an actual measurement frequency component extraction unit extracting the feature frequency component from an actual measurement vibration value, which is a value of the vibration measured by the vibration measuring unit at actual measurement timing that is the previously set initial measurement timing or later while the rotation device is operating;

a differential value calculating unit calculating a differential value between an initial frequency component, which is the feature frequency component extracted from the initial vibration value, and an actual measurement frequency component, which is the feature frequency component extracted from the actual measurement vibration value; and an abnormality diagnosis unit comparing the differential value calculated by the differential value calculating unit and a previously set diagnosis threshold, and diagnosing abnormality of each of the abnormality diagnosis targets based on a result of the comparison, wherein after the initial frequency component extraction unit extracts the initial frequency component, the vibration measuring unit measures the actual measurement vibration value every time rotation speed of the rotation shaft becomes the setting rotation speed, the actual measurement frequency component extracting unit extracts the actual measurement frequency component from the measured actual measurement vibration value, the differential value calculating unit calculates a differential value between the initial frequency component and the extracted actual measurement frequency component, and the abnormality diagnosis unit compares the calculated differential value and the diagnosis threshold and diagnoses abnormality of each of the abnormality diagnosis targets based on a result of the comparison.

9. The bearing according to claim 8 wherein
the rotation device is configured by including the bearing, the rotation shaft, and a rotor supported by the bearing, and
the abnormality diagnosis target is at least a constituent of the rotation device including the bearing, the rotation shaft, and the rotor.

10. The bearing according to claim 8 wherein
the initial frequency component extraction unit and the actual measurement frequency component extraction unit extract the feature frequency component by order analysis processing.

11. The bearing according to claim 8 wherein
when it is determined that the vibration measuring unit has measured the vibration for a period of time of previously set diagnosable time or longer at the initial measurement timing, the initial frequency component extraction unit carries out extraction processing of the initial frequency component with respect to the initial vibration value for the period of time of the diagnosable time or longer, and,
when it is determined that the vibration measuring unit has measured the vibration for a period of time of the diagnosable time or longer at the actual measurement timing, the actual measurement frequency component extraction unit carries out extraction processing of the actual measurement frequency component with respect to the actual measurement vibration value for the period of time of the diagnosable time or longer.

12. A rotation device, comprising:
an abnormality diagnosis device, wherein the abnormality diagnosis device comprises:

a vibration detecting unit detecting vibration venerated in the rotation device configured by including a bearing that supports a rotation shaft;

a rotation speed detecting unit detecting rotation speed of the rotation shaft;

a vibration measuring unit measuring vibration generated in the rotation device while the rotation shaft is rotating at previously set setting rotation speed, based on a detection result of the rotation speed detecting unit and a detection result of the vibration detecting unit;

an initial frequency component extraction unit extracting a feature frequency component regarding abnormality of each abnormality diagnosis target of the rotation device, from an initial vibration value, which is a value of the vibration measured by the vibration measuring unit at previously set initial measurement timing while the rotation device is operating;

an actual measurement frequency component extraction unit extracting the feature frequency component from an actual measurement vibration value, which is a value of the vibration measured by the vibration measuring unit at actual measurement timing that is the previously set initial measurement timing or later while the rotation device is operating;

a differential value calculating unit calculating a differential value between an initial frequency component, which is the feature frequency component extracted from the initial vibration value, and an actual measurement frequency component, which is the feature frequency component extracted from the actual measurement vibration value; and an abnormality diagnosis unit comparing the differential value calculated by the differential value calculating unit and a previously set diagnosis threshold, and diagnosing abnormality of each of the abnormality diagnosis targets based on a result of the comparison, wherein after the initial frequency component extraction unit extracts the initial frequency component, the vibration measuring unit measures the actual measurement vibration value every time rotation speed of the rotation shaft becomes the setting rotation speed, the actual measurement frequency component extracting unit extracts the actual measurement frequency component from the measured actual measurement vibration value, the differential value calculating unit calculates a differential value between the initial frequency component and the extracted actual measurement frequency component, and the abnormality diagnosis unit compares the calculated differential value and the diagnosis threshold and diagnoses abnormality of each of the abnormality diagnosis targets based on a result of the comparison.

13. The rotation device according to claim 12 wherein
the rotation device is configured by including the bearing, the rotation shaft, and a rotor supported by the bearing, and
the abnormality diagnosis target is at least a constituent of the rotation device including the bearing, the rotation shaft, and the rotor.

14. The rotation device according to claim 12 wherein
the initial frequency component extraction unit and the actual measurement frequency component extraction unit extract the feature frequency component by order analysis processing.

15. The rotation device according to claim 12 wherein
when it is determined that the vibration measuring unit has measured the vibration for a period of time of previously set diagnosable time or longer at the initial measurement timing, the initial frequency component extraction unit carries out extraction processing of the initial frequency component with respect to the initial vibration value for the period of time of the diagnosable time or longer, and,
when it is determined that the vibration measuring unit has measured the vibration for a period of time of the diagnosable time or longer at the actual measurement timing, the actual measurement frequency component extraction unit carries out extraction processing of the actual measurement frequency component with respect to the actual measurement vibration value for the period of time of the diagnosable time or longer.

16. An industrial machine, comprising:
an abnormality diagnosis device, wherein the abnormality diagnosis device comprises:
a vibration detecting unit detecting vibration venerated in a rotation device configured by including a bearing that supports a rotation shaft;
a rotation speed detecting unit detecting rotation speed of the rotation shaft;
a vibration measuring unit measuring vibration generated in the rotation device while the rotation shaft is rotating at previously set setting rotation speed, based on a detection result of the rotation speed detecting unit and a detection result of the vibration detecting unit;
an initial frequency component extraction unit extracting a feature frequency component regarding abnormality of each abnormality diagnosis target of the rotation device, from an initial vibration value, which is a value of the vibration measured by the vibration measuring unit at previously set initial measurement timing while the rotation device is operating;
an actual measurement frequency component extraction unit extracting the feature frequency component from an actual measurement vibration value, which is a value of the vibration measured by the vibration measuring unit at actual measurement timing that is the previously set initial measurement timing or later while the rotation device is operating;
a differential value calculating unit calculating a differential value between an initial frequency component, which is the feature frequency component extracted from the initial vibration value, and an actual measurement frequency component, which is the feature frequency component extracted from the actual measurement vibration value; and
an abnormality diagnosis unit comparing the differential value calculated by the differential value calculating unit and a previously set diagnosis threshold, and diagnosing abnormality of each of the abnormality diagnosis targets based on a result of the comparison,
wherein
after the initial frequency component extraction unit extracts the initial frequency component, the vibration measuring unit measures the actual measurement vibration value every time rotation speed of the rotation shaft becomes the setting rotation speed, the actual measurement frequency component extracting unit extracts the actual measurement frequency component from the measured actual measurement vibration value, the differential value calculating unit calculates a differential value between the initial frequency component and the extracted actual measurement frequency component, and the abnormality diagnosis unit compares the calculated differential value and the diagnosis threshold and diagnoses abnormality of each of the abnormality diagnosis targets based on a result of the comparison.

17. A vehicle, comprising:
an abnormality diagnosis device, wherein the abnormality diagnosis device comprises:
a vibration detecting unit detecting vibration generated in a rotation device configured by including a bearing that supports a rotation shaft;
a rotation speed detecting unit detecting rotation speed of the rotation shaft;
a vibration measuring unit measuring vibration generated in the rotation device while the rotation shaft is rotating at previously set setting rotation speed, based on a detection result of the rotation speed detecting unit and a detection result of the vibration detecting unit;
an initial frequency component extraction unit extracting a feature frequency component regarding abnormality of each abnormality diagnosis target of the rotation device, from an initial vibration value, which is a value of the vibration measured by the vibration measuring unit at previously set initial measurement timing while the rotation device is operating;
an actual measurement frequency component extraction unit extracting the feature frequency component from an actual measurement vibration value, which is a value of the vibration measured by the vibration measuring unit at actual measurement timing that is the previously set initial measurement timing or later while the rotation device is operating;
a differential value calculating unit calculating a differential value between an initial frequency component, which is the feature frequency component extracted from the initial vibration value, and an actual measurement frequency component, which is the feature frequency component extracted from the actual measurement vibration value; and
an abnormality diagnosis unit comparing the differential value calculated by the differential value calculating unit and a previously set diagnosis threshold, and diagnosing abnormality of each of the abnormality diagnosis targets based on a result of the comparison,
wherein
after the initial frequency component extraction unit extracts the initial frequency component, the vibration measuring unit measures the actual measurement vibration value every time rotation speed of the rotation shaft becomes the setting rotation speed, the actual measurement frequency component extracting unit extracts the actual measurement frequency component from the measured actual measurement vibration value, the differential value calculating unit calculates a differential value between the initial frequency component and the extracted actual measurement frequency component, and the abnormality diagnosis unit compares the calculated differential value and the diagnosis threshold and diagnoses abnormality of each of the abnormality diagnosis targets based on a result of the comparison.

* * * * *